(12) United States Patent
Möller

(10) Patent No.: US 7,136,492 B2
(45) Date of Patent: Nov. 14, 2006

(54) VISUAL OR AUDIO PLAYBACK OF AN AUDIOGRAM

(75) Inventor: Jonathan Möller, Kilchberg (CH)

(73) Assignee: Phonak AG, Stafa (CH)

( * ) Notice: Subject to any disclaimer, the term of this patent is extended or adjusted under 35 U.S.C. 154(b) by 309 days.

(21) Appl. No.: 10/193,613

(22) Filed: Jul. 11, 2002

(65) Prior Publication Data

US 2004/0008849 A1    Jan. 15, 2004

(51) Int. Cl.
*H04R 29/00* (2006.01)
*G10L 19/00* (2006.01)
*A61B 13/00* (2006.01)
*A61B 5/00* (2006.01)

(52) U.S. Cl. .................. 381/60; 600/558; 600/559; 704/200.1

(58) Field of Classification Search ................. 381/60; 600/558–559; 73/585
See application file for complete search history.

(56) References Cited

U.S. PATENT DOCUMENTS

| | | | | |
|---|---|---|---|---|
| 6,319,207 | B1 * | 11/2001 | Naidoo | 600/559 |
| 6,490,359 | B1 * | 12/2002 | Gibson | 381/119 |
| 6,602,202 | B1 * | 8/2003 | John et al. | 600/559 |
| 6,840,908 | B1 * | 1/2005 | Edwards et al. | 600/559 |

\* cited by examiner

*Primary Examiner*—Laura A. Grier
(74) *Attorney, Agent, or Firm*—Pearne & Gordon LLP

(57) ABSTRACT

A method for the visualization of the hearing capacity of a person. As a function of audiogram data, text is modified in any of several characteristics, including brightness, contrast, sharpness, and/or omission of letters.

19 Claims, 5 Drawing Sheets

VISUAL OR AUDIO PLAYBACK OF AN AUDIOGRAM

This invention relates to a method for visualizing the auditory faculty or hearing capacity of a person based on the visual or audio playback of an audiogram, to a method for graphically displaying the hearing capacity or hearing loss of a person, to a method for the audiographic measurement of the hearing capacity or hearing loss of a person, and to a web site featuring a module suitable for implementing the methods defined in this invention.

The hearing capacity or hearing loss of a person is usually measured by recording an audiogram of that person. Various pieces of literature also describe so-called simulation methods and procedures intended to determine the effect of ambient noise, clarity of enunciation, audio volume etc. on a person's auditory acuity. Reference is made to the articles written by Thomas Baer and Brian C. J. Moore titled "Effects of spectral smearing on the intelligibility of sentences in noise", and by Brian C. H. Moore and Brian R. Glasberg titled "Simulation of the effects of loudness recruitment and threshold elevation on the intelligibility of speech in quiet and in a background of speech".

However, no known method is offered by prior art that would enable a person, on the basis of a given audiogram or other hearing-related data, to determine for him- or herself the extent of his or her auditory deterioration, whether actual or potential. The same, of course, applies to a so-called healthy person who at least believes his or her hearing to be fully intact. Any such person is unable to have any sense of what hearing loss means. It may be of interest even to a healthy person to learn of the consequences of a hearing loss.

It is therefore the objective of this invention to provide a simple tool, a method, that enables a person to gauge and quantify his or her hearing capacity or hearing loss, as the case may be.

Recording a so-called audiogram may well be the best way to determine a person's hearing capacity. This is a graphic representation of the auditory acuity or lack thereof which is often associated with the so-called "recruitment", i.e. sensorineural deafness, whereby the person cannot hear "soft sounds" yet perceives "loud sounds" like anyone with "normal hearing". The audiogram can be recorded in individualized fashion. Audiograms can serve as graphic indications of the type and severity of a person's paracusis. The frequencies at which audiograms are usually recorded are as follows: 125 Hz, 250 Hz, 500 Hz, 1 kHz, 2 kHz, 4 kHz, 8 kHz. For each individual frequency, the threshold value is determined at which a person can still barely perceive an audio signal (threshold of audibility) which for a person with normal hearing is usually close to 0 dB. If those values are above a level of about 10–20 dB, they indicate a hearing loss. Of course it is possible to use different and/or additional frequency ranges.

In the attached graphs which will serve to explain in more detail how an audiogram is recorded, FIG. 1 shows an audiogram indicating characteristic audio signals, with letters identifying the individual frequency ranges;

Figure 1:
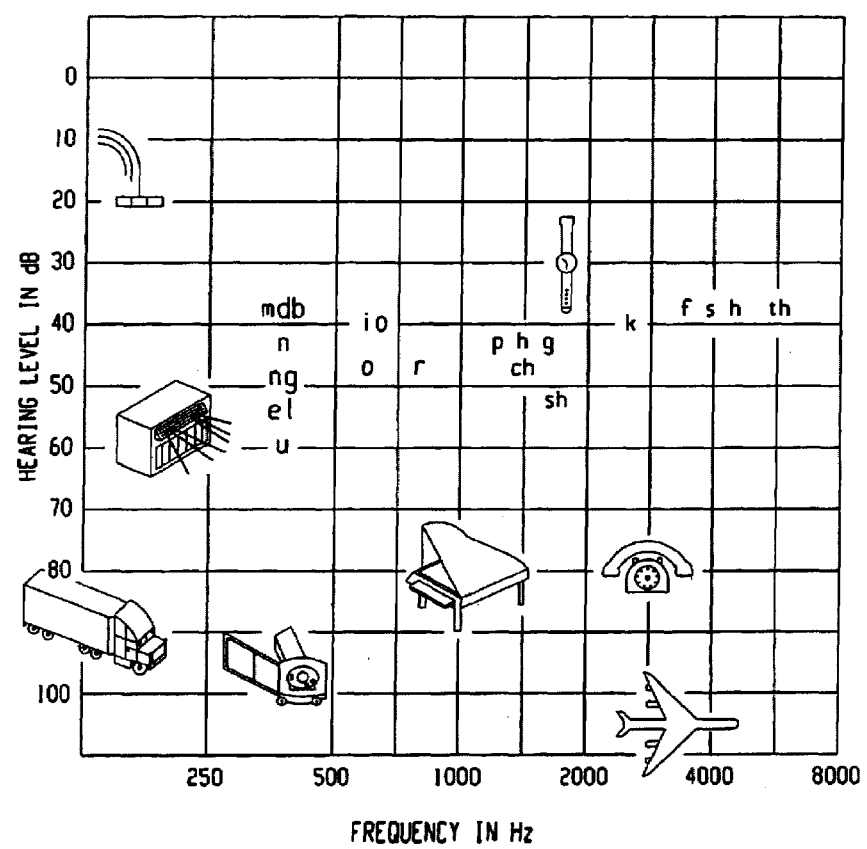

FIG. 1 will explain in some detail the way in which an audiogram is composed. As can be seen in FIG. 1, it is laid out as a coordinate system in which the y-axis represents the loudness-perception or hearing level while the x-axis indicates the various frequencies, where 250 Hz constitutes a low frequency and 8000 Hz a high frequency. Also symbolized in FIG. 1 are the signals characteristic of the various frequencies, such as the sound of a truck or of an engine in the range between 125 and 250 Hz, that of a lawn mower around 500 Hz, a piano at 1 kHz, the ringing of a telephone at 3 kHz, and a jet plane at around 4 kHz. The chirping of birds would register for instance between 4 and 8 kHz which is why persons with a hearing loss in the high frequency range usually cannot hear it.

But the loudness or hearing level is an important factor as well. In the audiogram per FIG. 1 it is represented by the y-axis where 0 dB is a very low level, 100 dB a very high level. For example, a clock may tick at a frequency of about 1800 Hz, yet very quietly at around 30 dB, making the ticking of the clock barely audible to a person with diminished hearing.

The letters in FIG. 1 correspond to the different frequencies as well as loudness levels. For example, the letter m, plotted in the range between 250 and 500 Hz, typically sounds at an intensity level lower than that of, say, the vowel e even though the latter is positioned in the same frequency range. In general, it is fair to say that vowels are found in frequency ranges lower than those for instance of sibilants such as s, the English th or the letter f.

Figure 2:
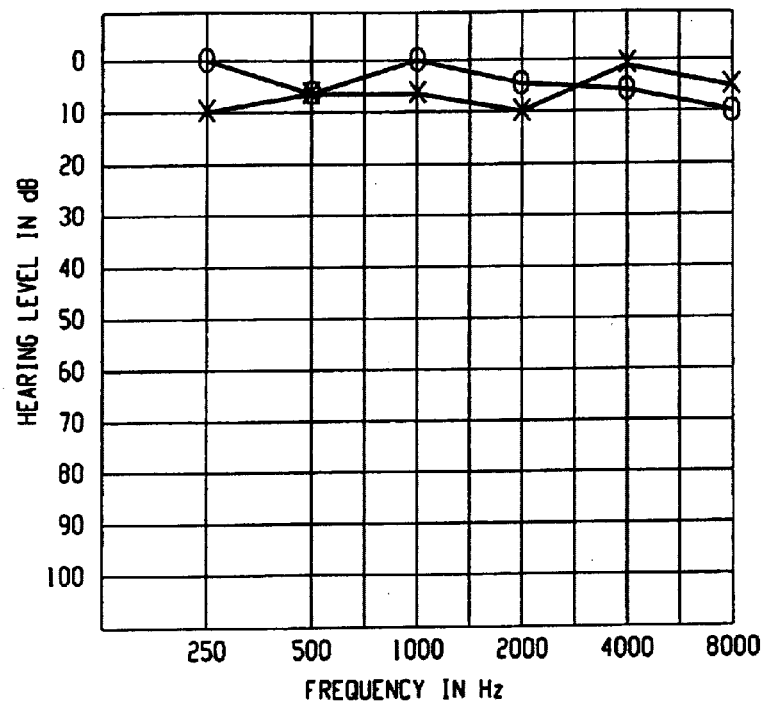
FIG. 2 is an audiogram of a person with normal hearing.

FIG. 2 illustrates a characteristic audiogram of a person with normal hearing, with separate audiograms recorded for the left ear and for the right ear as indicated in FIG. 2. The value for the left ear is identified as x, that for the right ear as o.

Figure 3:
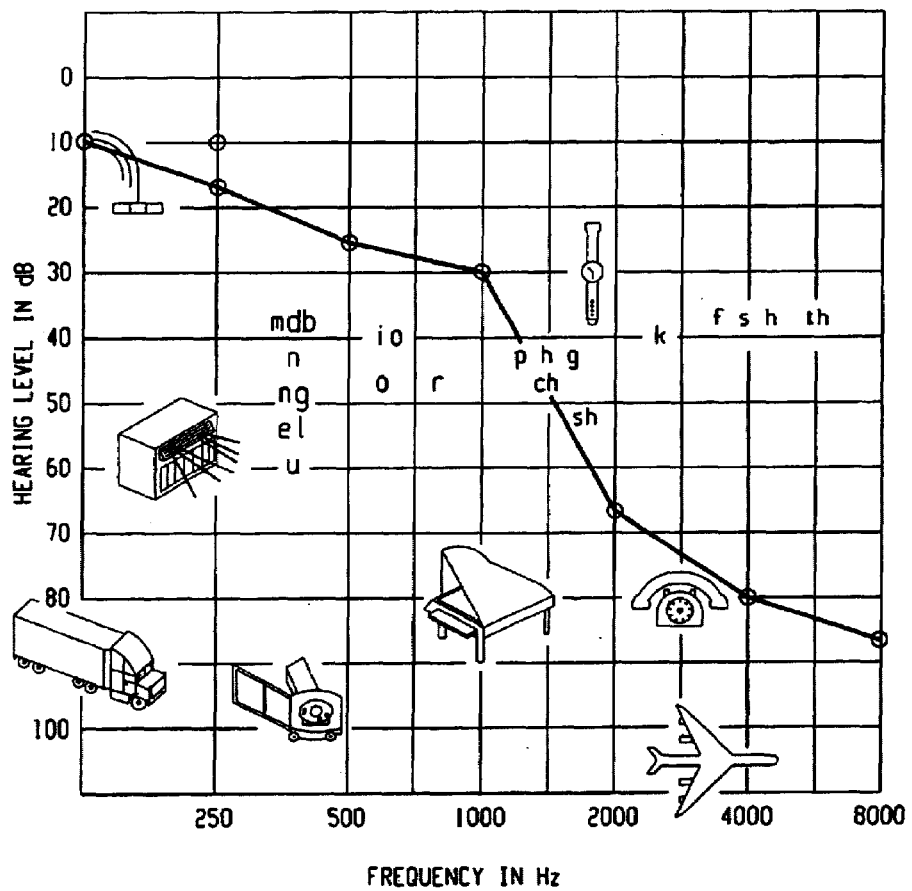
FIG. 3 is an example of an audiogram of a person with impaired hearing.

FIG. 3 is an audiogram of a person with impaired hearing. In this case, the hearing loss in the low frequency range is minimal whereas in the high frequency range it indicates a very high degree of paracousia.

The following are other examples of hearing loss:

Audiogram Example I: Minor hearing loss at high frequencies 10 dB, 10 dB, 10 dB, 15 dB, 20 dB, 30 dB, 45 dB.

Audiogram Example II: Moderate to severe hearing loss 30 dB, 30 dB, 30 dB, 50 dB, 80 dB, 90 dB, 75 dB Audiogram Example IIb: Another case of moderate to severe hearing loss 20 dB, 20 dB, 25 dB, 35 dB, 45 dB, 60 dB, 80 dB Audiogram Example III: Moderate hearing loss distributed over the entire frequency 50 dB, 55 dB, 55 dB, 50 dB, 60 dB, 65 dB, 65 dB The audiogram notwithstanding, it is important to realize that not all frequencies constitute the same value for hearing and understanding. The diagram in FIG. 4 reflects a so-called speech banana that yields information as to the key frequencies for understanding speech and those for perceiving loudness. Section A in the diagram accounts for 60% of loudness perception and only 5% for understanding. By contrast, section B accounts for only 40% of loudness perception while as much as 95% of understanding occurs in the frequency range from 1 to 4 kHz in section B. Section C may be considered the "comfort zone" insofar as that section is no longer important for the understanding of speech but is more responsible for the perception and discrimination of tonal qualities.

In other words, it is essentially the range from 1 to 4 kHz that accounts for speech intelligibility, i.e. the clarity of perception of the spoken word.

Figure 4:
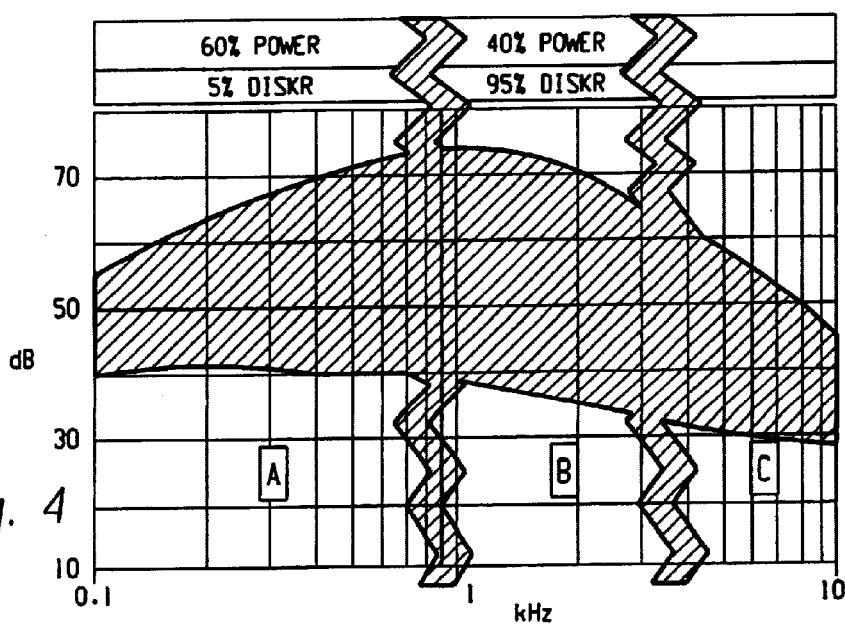
FIG. 4 is a diagram of a "speech banana"

This invention now proposes to include as factors in the visualization of the hearing capacity the audiogram, the loudness perception as well as speech intelligibility. In terms of loudness perception as well as intelligibility, the values that are largely identical for most people within a particular language area are fairly distributed over the various frequency ranges. Of course, these factors may differ from one language area to another, for instance the East Asian, the Arabic, the Indo-European and the Romance language areas. For example, for the Japanese and other cultures these factors must be suitably adapted. In this context it has been found that, as shown in FIG. 4, the importance of loudness perception is far greater in the low frequency range than in the high frequency range. In other words, impaired hearing at the low frequencies of 125, 250 and 500 Hz is substantially more significant than at 4 or 8 kHz. The typical proportional distribution has been found to be 20, 20, 20, 20, 15, 5, 0%.

Figure 5:
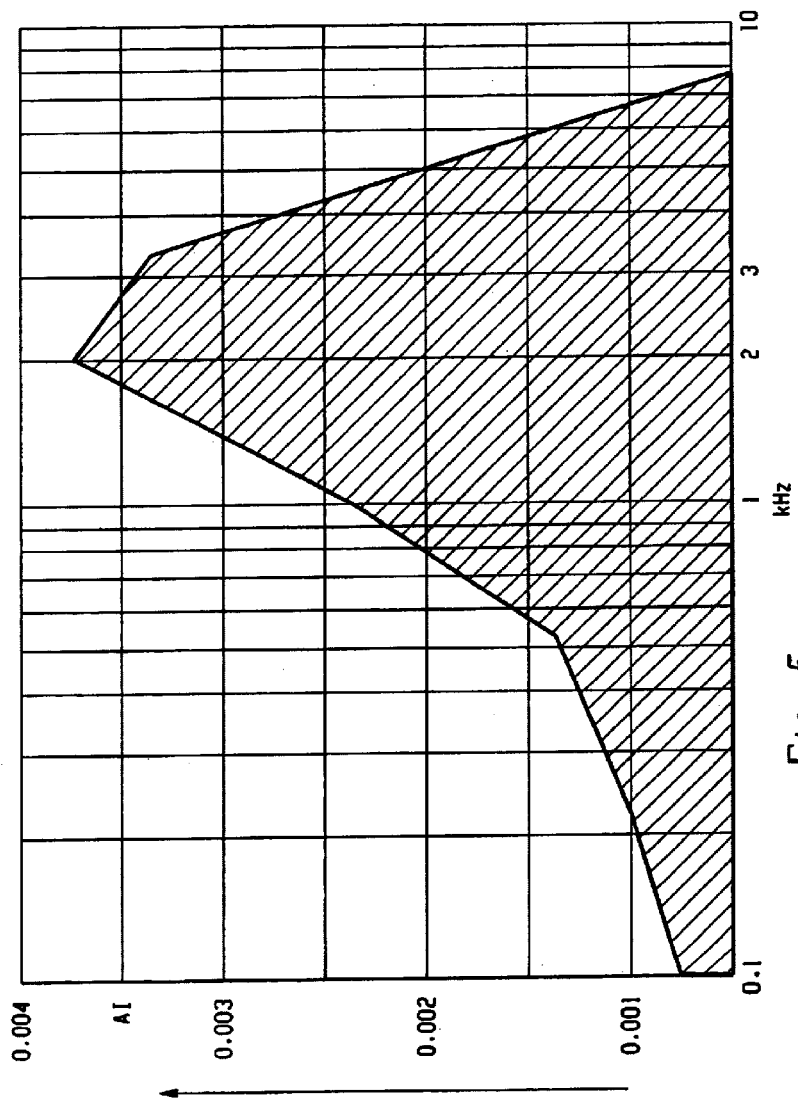
FIG. 5 is a diagram of speech intelligibility at different frequencies.

In contrast thereto, the intelligibility remains virtually unaffected at low and high frequencies while at medium frequencies, for example at 1 to 4 kHz, the negative effect on intelligibility is quite significant as shown in FIG. 5. The typical distribution has been found to be 0, 0, 5, 40, 40, 15, 0%.

Both value distributions add up to 100%, meaning that in proportional terms both loudness perception and overall clarity across the entire frequency range must be taken into account.

This invention now proposes to select a visual representation based on an audiogram i.e. on the audiographic data of a person as well as on loudness perception and clarity, i.e. the so-called articulation index, so as to convey to the viewer a visual impression for instance of the significance of a hearing loss. According to the invention, this visual representation is in the form of a textual display which is either a standard text or a text selectable by the user.

This text is modified on the basis of the audiogram, the loudness perception and the articulation index or speech intelligibility in a manner whereby its legibility changes as a function of the person's hearing capacity, i.e. of the pattern of the audiogram. The textual display changes in three different ways:

1. Brightness or contrast. Depending on loudness perception, the text is highly contrasted, meaning dark, for instance black on a white background, which signifies good hearing in terms of intensity. If the text is pale with poor contrast, it indicates correspondingly diminished (impaired) hearing.
2. Crispness of edge contours: Depending on speech intelligibility, the individual letters of the text will appear with corresponding clarity, i.e. crisply contoured, or fuzzy or illegible. For example, in the case of poor speech intelligibility, meaning poor auditory acuity relative to speech discrimination, the textual display will be fuzzy.
   1. Omission of individual letters: Depending on the pattern of the audiogram, individual letters of the text will be dropped altogether. In this connection, reference is made to FIG. 1 that contains individual letters within the coordinate representation of an audiogram. For example, if in reference to FIG. 3 a particular letter is positioned above the auditory curve in the diagram, that letter will be suppressed in the text while letters below that auditory curve will be displayed.

With these three textual display modes it is possible for a viewer to immediately determine the severity of his hearing loss, i.e. the extent to which his deafness has progressed. He has more than just one general, lumped answer in that the three aforementioned factors permit a differentiated analysis of the hearing impairment. By way of the aforementioned visualization it is thus possible, for example, to visually verbalize a statement by a hearing-impaired person saying "I can hear, but I don't understand a thing".

The specific example described below will explain the above-mentioned concept in more detail:

Let the assumption be an audiogram curve with the following parameters: At 125 Hz, 250 Hz, 500 Hz, 1 kHz, 2 kHz, 4 kHz, 8 kHz: 10 dB, 15 dB, 25 dB, 30 dB, 65 dB, 80 dB, 85 dB. The data correspond to the auditory curve in FIG. 3.

On the basis of the data in the auditory curve, Table 1 below serves to determine the hearing impairment relative to loudness as well as the hearing impairment relative to intelligibility:

TABLE 1

| Values from Auditory Curve | 10 | 15 | 25 | 30 | 65 | 80 | 85 | Total |
|---|---|---|---|---|---|---|---|---|
| Loudness Factor (%) | 20 | 20 | 20 | 20 | 15 | 5 | 0 | |
| "Loudness Hearing Impairment" (dB) value from auditory curve x loudness factor | 2 | 3 | 5 | 6 | 9.75 | 4 | 0 | 29.75 |
| Intelligibility Factor (%) | 0 | 0 | 5 | 40 | 40 | 15 | 0 | |
| "Intelligibility Hearing Impairment" (dB) = value from auditory curve y intelligibility factor | 0 | 0 | 1.25 | 12 | 26 | 12 | 0 | 51.25 |

According to Table 1, the hearing impairment relative to loudness is 29.75 dB, that relative to speech intelligibility or clarity is 51.25 dB.

In the visual presentation of these two factors the assumption is that the hearing capacity range is between 0 and 120 dB so that in the case of full loudness hearing capacity the letters near 0 will be completely black with maximum contrast while they are no longer visible at 120 dB. It follows that, the established value being 29.75 dB, the blackness of the textual display i.e. the corresponding contrast will diminish by about 25% ((29.75 dB/120 dB)×100%).

For speech intelligibility, 0 dB means crisply contoured letters while at 120 dB the letters will again be invisible. Hence, according to Table 1, the sharpness of the contours of the individual letters in this particular example will diminish by about 43% (51.25 dB/120 dB)×100%.

Figure 6:
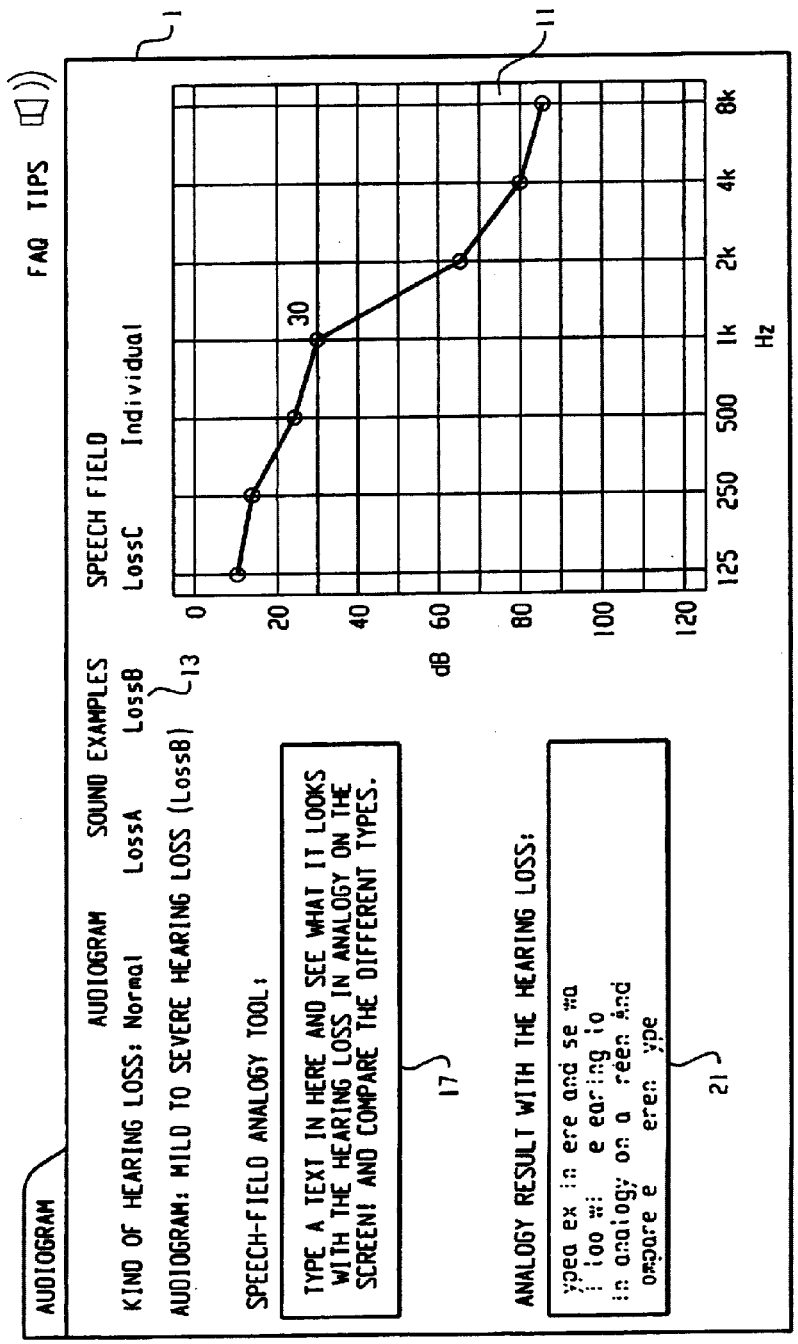
FIG. 6 is a text printout according to one example of the invention.

FIG. 6 includes a corresponding illustration of a text in line with the above explanations. That illustration may be a printout, for one example. The printout is generated following the input of the audiogram data for instance into a data processing system into which an appropriate software module was loaded, and the image is produced as a function of the data entered and of the parameters indicated above. In this particular printout, field 11 shows the audiogram and the seven frequency ranges as well as the dB values reflecting the hearing loss at the various frequencies.

Field 13 permits the setting of the hearing capacity or hearing loss or the selection of specified audiogram curves, or even an individualized entry on the basis of which the audiogram in field 11 is generated. In the case of this example a predefined audiogram curve was selected that corresponds to a hearing loss b and is reflected in the graph per field 11.

Field 17 contains a text that is to be processed on the basis of the data in the audiogram. Finally, field 21 shows the resulting text, simulating the auditory acuity of the person with the hearing impairment as reflected in the graph in field 11. The text in field 21 is paler compared to the original text in field 17, to an extent where the letters are no longer black but represent a grey level reflecting the 29.75 dB "loudness hearing impairment". The edges as well are poorly defined, reflecting the 51.25 "intelligibility impairment". Finally, various letters have dropped out, for instance the letters t, s, th and f. In this context reference is made to FIG. 3 where it is evident that the letters concerned are positioned above the auditory curve in the audiogram shown in field 11.

By means of an appropriate software package or software module it is also possible, of course, to interactively generate on a PC monitor a display corresponding to FIG. 6 by inputting the audiogram data that will produce a screen image identical to FIG. 6. But in lieu of a software package in the user's own PC it is equally possible to access via the Internet a website that stores a corresponding audiogram module. An audiogram module of that nature serves two purposes:

1. It displays the structure and functionality of an auditory threshold in the form of a technical visualization of a hearing loss.
2. It permits the visual display of what in the case of a hearing loss remains as a perceptible text.

The text reflects the change in perceptibility by the following:
a) the inaudible sounds or letters contained therein are filtered out;
b) the auditory intensity loss is reflected by corresponding grey levels; and
c) clarity levels are indicated by degrees of fuzziness.

A web-resident audiogram module of that nature is interactive. Apart from the predefined examples it permits the definition of one's own audiogram and playing with one's own texts. In other words, selecting a standard text is not imperative; instead, the user can enter his own text which will then appear in field 17.

The purpose of that type of audiogram module, apart from instructing the user relative to the functional modality of an auditory-threshold audiogram, is to permit casual, exploratory familiarization with the auditory consequences associated with a hearing loss. The analogous correlation of hearing and seeing makes it possible even for a hearing-impaired person to fathom the impact and extent of his hearing loss.

An audiogram module of that type further makes it possible to also gauge for instance the effect of ambient noise by an appropriate selection of the background color in field 21. In the absence of any ambient noise, the background color or shade selected for field 21 will be white or bright. As a function of the increase in ambient noise, for instance in a railroad station, in a workshop with machines running or even at home while a household appliance is in operation, different grey levels can be selected for the background, ranging from bright to dark. The louder the noise, the darker the background. Obviously, the legibility of the text will degrade as the background gets darker as a function of the increase in the loudness of the ambient noise. Here again, various predefined simulation values can be integrated in the audiogram module for selection by a user along the line of input option 13. And here again, individualized selection is possible. In reference to FIG. 6 it should be added that, of course, the user does not necessarily have to work with an audiogram that is divided into seven frequency ranges as shown. Instead, it is entirely possible to select different audiograms with a different set of frequency ranges. The same applies to the percentage distribution of the loudness factor and of the intelligibility factor, which distribution must necessarily be adapted to the values and number of the frequency ranges selected.

Recognizing a hearing loss does not absolutely require a textual display or visualization but may employ acoustic means as well. This invention therefore proposes storing in the audiogram module a sound sample, for instance music or spoken words, or a musical sound or voice sample entered by a user which will be processed and altered in the same way as a preselected or "canned" audiogram. In this case as well, the specified values relative to intensity loss or loudness hearing impairment and speech intelligibility will be taken into account. The data entered will modify the audio sample and play it back modified, reflecting in the case of a hearing impairment an intensity reduction as well as a reduction in clarity. In the case of music, for example, either the bass or the treble tones may drop out or may be only minimally perceptible. Especially when the user enters his own sound sample is it important for the audiogram module to capture the user's actual auditory capacity, i.e. his basic hearing must be determined first since otherwise the sample may possibly be played back in skewed fashion. Equally important for the determination of the "basic hearing capacity" are the tonal quality of the sound sample, the speakers, the PC, the sound card etc. The calibration can be performed for instance in that the audiogram module generates a key tone, a basic background noise or some other suitable signal that is perceptible with normal hearing. By turning up the volume for instance of a speaker the user can determine his basic hearing level in that he increases the volume until he hears the background noise. At that juncture the music sample or voice sample can be entered. The playback based on the audiogram will reflect the hearing capacity of the user for instance at a reduced level, giving the user an auditory measure of his hearing or of the state of progression of his hearing impairment.

Preferably, this audio presentation of the user's hearing capacity is again implemented by means of an audiogram module accessed at a website via the Internet but, of course, it can also be processed and displayed with the aid of a corresponding software module installed in the user's own PC.

The speech field, illustrated in FIG. 6, is important primarily to persons with diminished hearing while the playback of music or sound samples is of interest especially to persons with normal hearing.

The invention claimed is:

1. A method for visualization of a hearing capacity of a person, comprising the steps of:
   using audiogram data to modify a text sample in its brightness or its contrast against its background, in the sharpness of its contours, and/or through the total omission of individual letters, and displaying the modified text.

2. The method as in claim 1, wherein a loudness perception is reflected as a function of the brightness or contrast selected, wherein for good loudness perception characters of the text are caused to appear dark and sharply contrasted while, in analogous fashion, for poor loudness perception the characters are caused to appear light to completely faded with correspondingly diminished contrast.

3. The method as in claim 2, wherein the clarity of perception is reflected in the sharpness of the contours of the text, wherein for clear perception the characters are caused to appear sharply contoured while for poor perception the characters appear poorly defined or fuzzy.

4. The method as in claim 1, further comprising the complete removal of individual letters of the text when on the basis of frequency-allocated auditory values in the audiogram and due to an existing hearing level such letters are partly or entirely imperceptible.

5. The method as in claim 1, wherein the audiogram comprises a predefined number of frequency ranges, it includes intensity levels from 1 to 120 dB, that a loudness perception subdivided and distributed over the frequencies adds up to 100%, that auditory or hearing-loss values entered in dB are multiplied by the corresponding percentages in the respective frequency range, and that the values are totaled with the resulting sum constituting the basis for determining the brightness or contrast of text characters on a scale from 0 dB=dark or black or maximum contrast to 120 dB=white or without contrast.

6. The method as in claim 1, wherein the audiogram comprises a predefined number of frequency ranges, that it includes loudness levels from 0 to 120 dB, that a speech intelligibility perception subdivided and distributed over the frequencies adds up to 100%, that individual auditory or hearing-loss values are multiplied by the corresponding frequencies, that the values taken together result in a composite value for the speech intelligibility perception, and that the contour sharpness of text characters is determined accordingly on a scale from 0 dB=sharply contoured characters to 120 dB=fuzzy to unrecognizable characters.

7. An audiogram module for an Internet-accessed website, characterized in that it permits a visualization of an audiogram by the method per claim 1, wherein a person who has accessed the website can either select predefined reference audiograms or enter individualized audiogram hearing-level data for the purpose of editing and/or visualizing a predefined text or an individually entered text by said method.

8. The module as in claim 7, further comprising predefined audiograms for levels ranging from normal hearing to minor hearing impairment to severe hearing impairment with the hearing data variously weighted for low, medium and high frequencies.

9. The module as in claim 8, wherein the module permits the use of predefined audiograms for different language groups.

10. The module as in claim 7, wherein the conversion in the module occurs on the basis of significant values, with an adaptation in each case to the respective loudness and fading factor or to an articulation index through loudness- and fading-factor weighting in the individual frequency ranges based on the following values: 20, 20, 20, 20, 15, 5, 0% and through an adaptation for the following articulation-index values: 0, 0, 5, 40, 40, 15, 0%.

11. The module as in claim 7, wherein predefined ambient-condition-related values are accessible from the website and that these are factored into a background selection formula, wherein for the playback of the modified text they can be reflected by different grey levels.

12. An application of the method per claim 1, for visual recognition of a user's own hearing capacity or of a simulated hearing level.

13. A method for an audio playback based on an audiogram, comprising the steps of:
using audiogram data to modify intensity, loudness and/or clarity of an audio sample to reflect hearing of a user as recorded in the audiogram, and playing back the modified audio sample,
wherein the method further comprises using the audiogram data to modify the brightness or contours of a visual sample, and displaying the modified visual sample.

14. The method as in claim 13, wherein the audio sample is modified as a function of the audiogram hearing data, of loudness and fading factors and of an articulation index, reflected in the loudness and/or clarity of the sample.

15. An audiogram module for use with software programs stored in a computer or for an Internet-accessed website, suitable for implementing the method per claim 14, wherein a predetermined music or speech sample, or a music or speech sample entered by a user of the website, is modified and played back in modified form as a function of the audiogram hearing data, of the loudness and fading factor and of the articulation index.

16. The audiogram module as in claim 15, wherein a basic hearing level of the user is determined, and the playback of an audio sample calibrated, by means of an audio signal, thus setting a baseline value and a reference point for the calibration.

17. An application of the method per claim 13, for auditory recognition of a user's own hearing capacity or of a simulated hearing level.

18. A method for audio recognition of a hearing capacity of a person, comprising the steps of:
using audiogram data to modify at least one characteristic of an audio sample to reflect hearing of the person as recorded in the audiogram data, said characteristic is selected from the group consisting of intensity, loudness, or clarity of the audio sample;
and playing back the modified audio sample,
wherein the method further comprises using the audiogram data to modify the brightness or contours of a visual sample, and displaying the modified visual sample.

19. A method for visualization of a hearing capacity of a person comprising the steps of:
using audiogram data to modify at least one characteristic of a visual sample to reflect either normal hearing or diminished hearing of the person, said characteristic is selected from the group consisting of brightness, contrast against background, sharpness of visual sample contours, or through total omission of individual parts of the visual sample; and
displaying the modified visual sample.

\* \* \* \* \*